United States Patent
Claus et al.

(10) Patent No.: US 6,990,169 B2
(45) Date of Patent: Jan. 24, 2006

(54) METHOD AND SYSTEM FOR VIEWING A RENDERED VOLUME

(75) Inventors: Bernhard Erich Hermann Claus, Niskayuna, NY (US); Jeffrey Wayne Eberhard, Albany, NY (US)

(73) Assignee: General Electric Company, Schenectady, NY (US)

( * ) Notice: Subject to any disclaimer, the term of this patent is extended or adjusted under 35 U.S.C. 154(b) by 126 days.

(21) Appl. No.: 10/744,030

(22) Filed: Dec. 23, 2003

(65) Prior Publication Data

US 2005/0135557 A1    Jun. 23, 2005

(51) Int. Cl.
*A61B 6/03* (2006.01)
(52) U.S. Cl. .................... 378/4; 378/901; 382/131
(58) Field of Classification Search ............ 378/4, 378/8, 15, 19, 901; 382/131; 250/363.04, 250/363.05, 370.09
See application file for complete search history.

(56) References Cited

U.S. PATENT DOCUMENTS 4,885,688 A * 12/1989 Crawford ................ 345/427
6,845,144 B2 * 1/2005 Nishide et al. ............ 378/15

* cited by examiner

*Primary Examiner*—David V Bruce
(74) *Attorney, Agent, or Firm*—Fletcher Yoder

(57) ABSTRACT

A technique is provided for viewing a series of volumes that may be rendered using visualization techniques incorporating one or more weighting functions, such as depth-dependent weighting functions. In one aspect, the viewing technique may utilize such weighting functions to vary the volume of interest in a series of volume renderings. In addition, the viewing technique may provide for varying the viewing angle to minimize the effect of orientation specific artifacts in the displayed images.

33 Claims, 2 Drawing Sheets

METHOD AND SYSTEM FOR VIEWING A RENDERED VOLUME

BACKGROUND OF THE INVENTION

The present invention relates generally to the field of medical imaging, and more specifically to the field of tomosynthesis. In particular, the present invention relates to the visualization of reconstructed volumes from data acquired during tomosynthesis.

Tomosynthesis is an imaging modality that may be used in a medical context to allow physicians and radiologists to non-invasively obtain three-dimensional representations of selected organs or tissues of a patient. In tomosynthesis, projection radiographs, conventionally known as X-ray images, are acquired at different angles relative to the patient. Typically, a limited number of projection radiographs are acquired over a relatively small angular range. The projections comprising the radiographs generally reflect interactions between x-rays and the imaged object along the respective X-ray paths through the patient and, therefore, convey useful data regarding internal structures. From the acquired projection radiographs, a three-dimensional volumetric image representative of the imaged volume may be reconstructed.

The reconstructed volumetric image may be reviewed by a technologist or radiologist trained to generate a diagnosis or evaluation based on such data. In such a medical context, tomosynthesis may provide three-dimensional shape and location information of structures of interest as well as an increased conspicuity of the structures within the imaged volume. Typically, the structures within the reconstructed volumetric image, or within a slice, have a significantly higher contrast than in each of the respective projection images, i.e., radiographs.

However, evaluating the three-dimensional volumetric image may pose challenges in clinical practice. For example, viewing the volumetric image slice by slice may require viewing forty to sixty slices or more. Therefore, small structures present in a single slice may be easily missed. Moreover, the three-dimensional position and shape information, in particular the depth information (i.e., essentially in the direction of projection for the data acquisition), is only implicitly contained in the stack of slices, with the "depth" of a structure that is located within a given slice being derived from the position of that slice within the full slice sequence or the volumetric image.

To address these problems, three-dimensional volume visualization or volume rendering may be employed. These visualization techniques attempt to show the full three-dimensional volumetric image simultaneously, with the location and shape information being conveyed mainly through changes in view angle, i.e., perspective. In addition, volume visualization may be enhanced by including an occlusion effect, which hides (or partially hides) structures that are located behind other structures, depending on the view angle.

However, one drawback of many volume rendering methods is an associated loss of contrast, which may more than offset gains in contrast achieved by the three-dimensional reconstruction process. This problem typically occurs when showing the full volume from a view angle requires some type of averaging of values of the volumetric image for a range of depths. As a result, the perceived contrast of a small structure may be significantly smaller in the rendered image than in the original projection image data set. In addition, if a structure of interest is not located "close to the viewpoint," i.e., in front of most other structures, as seen from the viewpoint, occlusion effects may further diminish the contrast of the structure, or even hide it completely. This problem may be addressed by visualizing, i.e., rendering, only the region or volume of interest within the volumetric image. This technique, however, requires either a priori knowledge of the volume of interest or an intelligent way of continuously adjusting the volume of interest during the volume rendering process to allow the visualization of any subvolume of the full reconstructed volumetric image. A technique for visualizing three-dimensional tomosynthesis data that provides good visualization of the three-dimensional context, i.e., localization and space information, without reducing contrast may, therefore, be desirable. Similarly, viewing modes which take advantage of the properties of such visualization techniques may also be desirable.

BRIEF DESCRIPTION OF THE INVENTION

The present technique provides a novel approach to visualizing three-dimensional data, referred to as volumetric images, such as data provided by tomosynthesis imaging systems. In particular, the present technique provides for the use of weighting functions, such as depth-dependent weighting functions, in the determination of pixel values in the volume rendered image from voxel values in the volumetric image. Weighting functions may modify the voxel value itself and/or other modifiers of the voxel value, such as opacity functions. Furthermore, the technique provides for novel viewing modes, such as varying the volume of interest via the weighting function or functions. Other novel viewing modes may include varying the view angle to reduce artifacts attributable to the scan trajectory and simultaneously displaying different volume renderings with common reference image data but different perspectives.

In accordance with one aspect of the technique, a method is provided for viewing a sequence of rendered volume images. In accordance with this aspect, a volume of interest comprising reconstructed three-dimensional volumetric image data is selected. A reference depth may be varied which affects the operation of one or more weighting functions used to render volume images representing the volume of interest.

In accordance with another aspect of the technique, a method is provided for viewing a sequence of rendered volume images. In accordance with this aspect, a volume comprising reconstructed three-dimensional volumetric image data is selected. A view angle for rendering volume images of the volume may then be varied such that the visual presence of one or more orientation specific image artifacts is reduced. Systems and computer programs that afford functionality of the type defined by these aspects are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

In the field of medical imaging, various imaging modalities may be employed to non-invasively examine and/or diagnose internal structures of a patient using various physical properties. One such modality is tomosynthesis imaging which utilizes a limited number of projection radiographs, typically twenty or less, each acquired at a different angle relative to a patient. The projection radiographs may then be combined to generate a volumetric image representative of the imaged object, i.e., a three-dimensional set of data that provides three-dimensional context and structure for the volume of interest. The present technique addresses visualization issues that may arise in the display of volumetric images provided by tomosynthesis imaging. In particular, the present technique allows for the incorporation of weighting into the visualization process and for various viewing modes that may benefit from such weighting.

Figure 1:
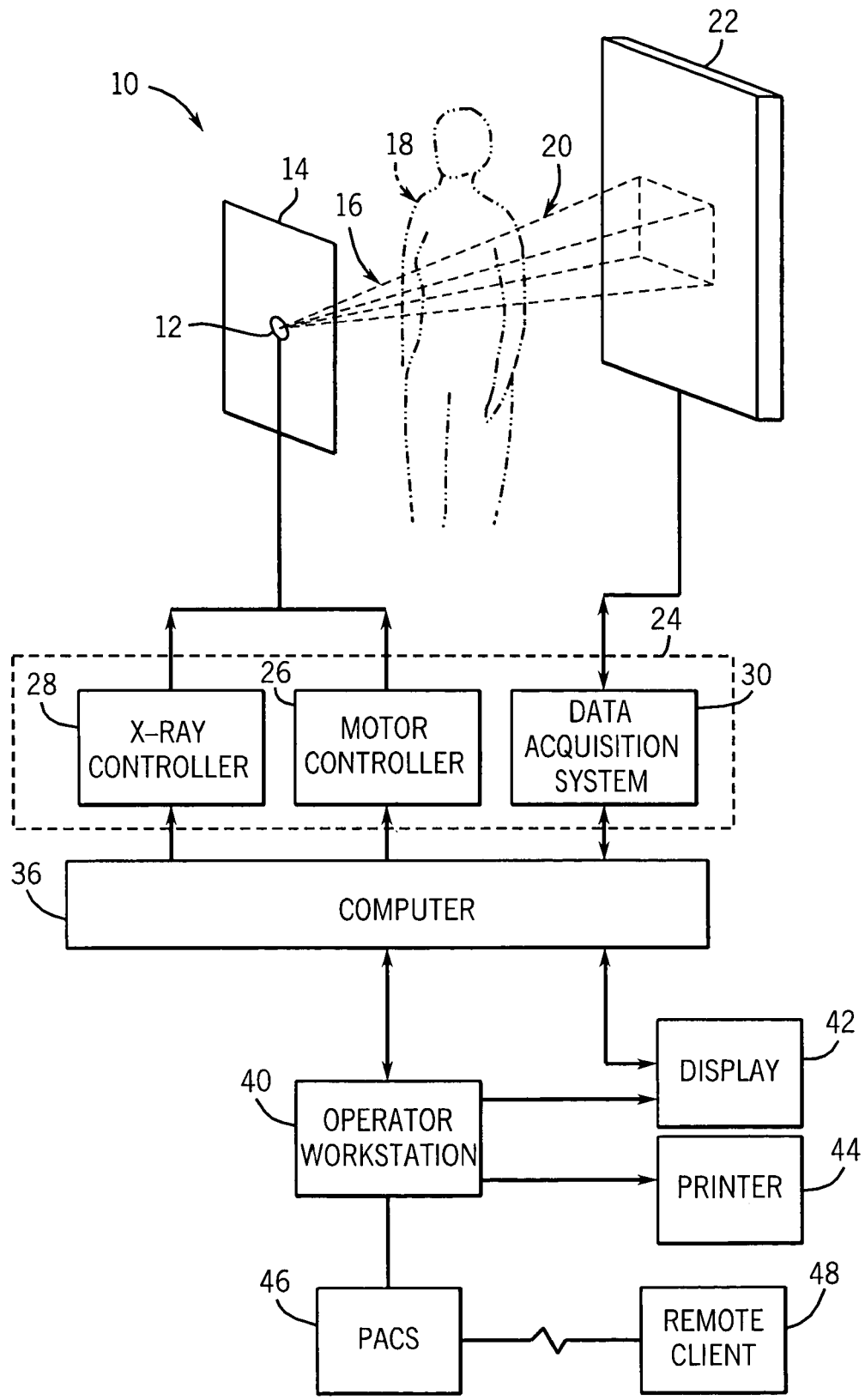
FIG. 1 is a diagrammatical view of an exemplary imaging system in the form of a tomosynthesis imaging system for use in providing volumetric images and producing visualizations of the volumetric images in accordance with aspects of the present technique.

An example of a tomosynthesis imaging system 10 capable of acquiring and/or processing image data in accordance with the present technique is illustrated diagrammatically in FIG. 1. As depicted, the tomosynthesis imaging system 10 includes an X-ray source 12, such as an X-ray tube and associated components, e.g., for support and filtering. The X-ray source 12 may be moved within a constrained region. As one of ordinary skill in the art will appreciate, the constrained region may be arcuate or otherwise three-dimensional. For simplicity, however, the constrained region is depicted and discussed herein as a plane 14 within which the source 12 may move in two-dimensions. Alternatively, a plurality of individually addressable and offset radiation sources may be used.

A stream of radiation 16 is emitted by the source 12 and passes into a region in which a subject, such as a human patient 18, is positioned. A portion of the radiation 20 passes through or around the subject and impacts a detector array, represented generally at reference numeral 22. The detector 22 is generally formed by a plurality of detector elements, generally corresponding to pixels, which produce electrical signals that represent the intensity of the incident X-rays. These signals are acquired and processed to reconstruct a volumetric image representative of the features within the subject. A collimator may also be present, which defines the size and shape of the X-ray beam 16 that emerges from the X-ray source 12.

Source 12 is controlled by a system controller 24 which furnishes both power and control signals for tomosynthesis examination sequences, including positioning of the source 12 relative to the patient 18 and the detector 22. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system 10 to execute examination protocols and to acquire the resulting data.

In the exemplary imaging system 10, the system controller 24 commands the movement of the source 12 within the plane 14 via a motor controller 26, which moves the source 12 relative to the patient 18 and the detector 22. In alternative implementations, the motor controller 26 may move the detector 22, or even the patient 18, instead of or in addition to the source 12. Additionally, the system controller 24 may include an X-ray controller 28 to control the activation and operation of the X-ray source 12. In particular, the X-ray controller 28 may be configured to provide power and timing signals to the X-ray source 12. By means of the motor controller 26 and X-ray controller 28, the system controller 24 may facilitate the acquisition of radiographic projection images at various angles through the patient 18.

The system controller 24 may also include a data acquisition system 30 in communication with the detector 22. The data acquisition system 30 typically receives data collected by readout electronics of the detector 22, such as sampled analog signals. The data acquisition system 30 may convert the data to digital signals suitable for processing by a processor-based system, such as a computer 36.

The computer 36 is typically coupled to the system controller 24. The data collected by the data acquisition system 30 may be transmitted to the computer 36 for subsequent processing, reconstruction and volume rendering. For example, the data collected from the detector 22 may undergo correction and pre-processing at the data acquisition system 30 and/or the computer 36 to condition the data to represent the line integrals of the attenuation coefficients of the scanned objects. The processed data, commonly called projections, may then be used as input to a reconstruction process to formulate a volumetric image of the scanned area. Once reconstructed, the volumetric image produced by the system of FIG. 1 reveals an internal region of interest of the patient 18 which may be used for diagnosis, evaluation, and so forth. Computer 36 may also compute volume rendered images of the reconstructed volumetric image, which may then be displayed on display 42. In an alternative embodiment, some functions of the computer 36 may be carried out by additional computers (not shown), which may include specific hardware components, such as for fast three-dimensional reconstruction or volume rendering.

The computer 36 may comprise or communicate with memory circuitry that can store data processed by the computer 36 or data to be processed by the computer 36. It should be understood that any type of computer accessible memory device capable of storing the desired amount of data and/or code may be utilized by such an exemplary system 10. Moreover, the memory circuitry may comprise one or more memory devices, such as magnetic or optical devices, of similar or different types, which may be local and/or remote to the system 10. The memory circuitry may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe acquired projection images, reconstructed volumetric images and other data relevant to the system from computer 36, initiate imaging, and so forth.

A display 42 coupled to the operator workstation 40 may be utilized to observe the reconstructed volumetric images and to control imaging. Additionally, the images may also be printed by a printer 44 that may be coupled to the operator workstation 40. The display 42 and printer 44 may also be connected to the computer 36, either directly or via the operator workstation 40. Further, the operator workstation 40 may also be coupled to a picture archiving and communications system (PACS) 44. It should be noted that PACS 44 may be coupled to a remote system 46, radiology department information system (RIS), hospital information system (HIS) or to an internal or external network, so that others at different locations may gain access to the image and to the image data.

It should be further noted that the computer 36 and operator workstation 40 may be coupled to other output devices that may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Once reconstructed and combined, the volumetric image data generated by the system of FIG. 1 reveal the three-dimensional spatial relationship and other characteristics of internal features of the patient 18. To convey useful medical information contained within the image data, a visualization technique may be employed to represent aspects of the image data to a technologist or radiologist. For example, in traditional approaches to diagnosis of medical conditions, a radiologist might review one or more slices of the volumetric image data, either on a printed medium, such as might be produced by the printer 44, or on the display 42. Features of interest might include nodules, lesions, sizes and shapes of particular anatomies or organs, and other features that may be discerned in the volumetric image data based upon the skill and knowledge of the individual practitioner.

Other analyses may be based upon a volume rendering or visualization technique that allows for the simultaneous viewing of the full three-dimensional data set. Such techniques allow three-dimensional location and shape information to be conveyed in a more natural and intuitive way than in slice viewing, though with a possible reduction in the contrast of small structures. In particular, depth information within the rendered or visualized volume may be conveyed through the perceived relative motion of structures when changing perspectives, i.e., view angles. Furthermore, occlusion effects may be introduced to convey the depth ordering of structures at a particular perspective, further enhancing the perception of depth. In conjunction with occlusion effects, the degree of transparency of structures may be adjustable to allow control of the depth of penetration when viewing the image data. In addition to varying perspective to facilitate the perception of depth, the volume of interest may also be adjusted to exclude structures from the rendered image and/or to optimize the contrast of small structures in the rendered image.

Figure 2:
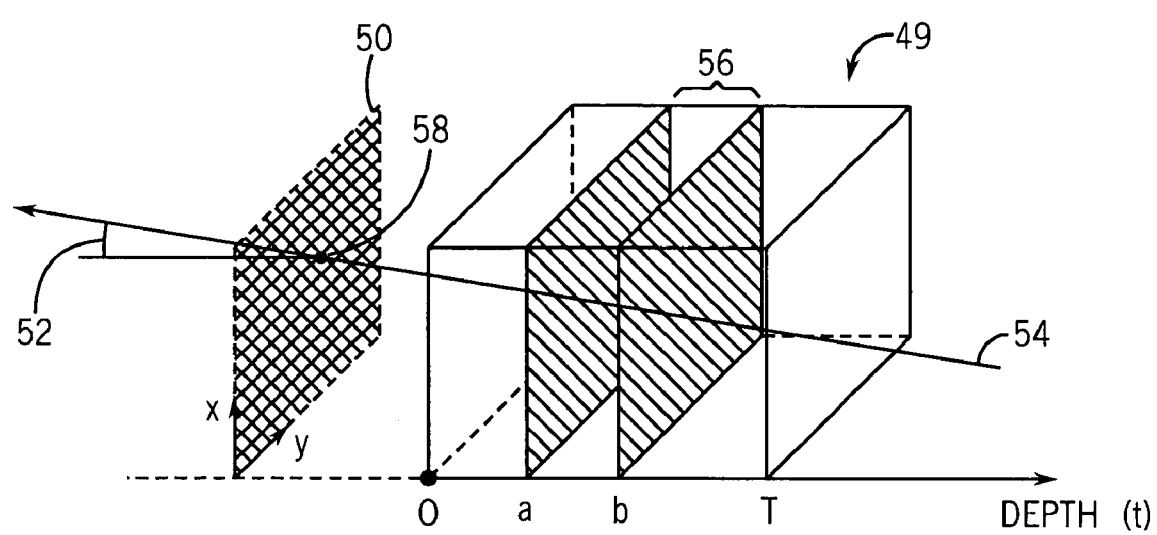
FIG. 2 depicts an exemplary volumetric image and the aspects of the volumetric image as they relate to three-dimensional visualization.

For example, referring to FIG. 2, a volume rendered image for a reconstructed volumetric image 49 may be generated by specifying a view angle 52, associated with the desired viewpoint, and an image plane 50, which may or may not be parallel to the respective slices of the volumetric image data. The intensity values associated with the intersection of a ray 54 and the volume of interest 56 may then be projected onto a corresponding pixel 58 of the image plane 50. In particular, the intensity value of a pixel 58 in the rendered image may be derived from some functional relationship of the intensity values, or other signal properties, of the reconstructed volumetric image 49 at locations along the ray. As one of ordinary skill in the art will appreciate, the ray 54 is associated with a particular viewing direction, which may determine such things as the ordering of values in an associated volume rendered image.

For example, the intensity or gray scale value, r, of a pixel in the rendered volume may be given by the equation:

$$r = \int_a^b w(t) \cdot e^{-\int_0^t o(s)ds} dt, \qquad (1)$$

where both integrals are path integrals of values that are functions of the values, v, of the three-dimensional volumetric image data set at the corresponding locations, i.e., w(t) is not a function of, t, but of, v(t). Thus, the opacity, o, and the value w depend on the corresponding volumetric image values, v, their functional relationship being defined by suitable transfer functions. While FIG. 2 suggests that equation (1) is parameterized in terms of the depth, t, in standard volume rendering t represents the path length along the considered ray 54. For small view angles, however, these parameterizations are essentially equivalent.

As one of ordinary skill in the art will appreciate, equation (1) generates a pixel value in the rendered image where the contribution of each voxel value along the ray 54 is weighted by the opacity, o, associated with all voxels in front of it. Indeed, the opacity term in equation (1), when discretized, introduces a multiplicative weighting of: $e^{-(a+b)} = e^{-a} \cdot e^{-b}$. Therefore, a volume-rendered image, r(x,y), may be created by evaluating equation (1) for all rays 54, defined by the associated image pixel 58 coordinates (x, y), corresponding to the specified view point, view angle 52 and image plane 50.

In practice, various visualization geometries may be employed. For example, in parallel projection geometry all rays 54 are assumed to be parallel and the view angle 52 is the angle of the rays 54 through the volumetric image 49. Conversely, in cone beam geometry, the rays 54 are assumed to all go through a common point and the view angle 52 can be defined as the angle of that viewpoint with respect to some reference point in the image. The present technique may be utilized with parallel projection or cone beam geometries as well as with other rendering geometries that may be employed. In addition to the rendering process described, other data conditioning and/or normalization processes may be performed, such as normalization by total pathlength through the volume of interest 56, |b−a|, which do not affect the implementation of the present technique.

The preceding discussion and equation (1) generally relate to the visualization technique known as composite ray-casting. Special cases of equation (1) may correspond to other visualization techniques, however. For example, a zero-opacity case generally corresponds to what is known as an X-ray projection viewing mode. Similarly, if the volume of interest is defined by depths a and b that are close, such as where |b−a| is constant, the visualization mode is known as thick slice viewing. In cases where the interval [a,b] encompasses only a single slice, i.e., slice-by-slice viewing, the visualization method corresponds to a slice viewing mode. Other visualization modes may also be utilized, such as maximum or minimum intensity projection. As noted above, these various visualization techniques may present difficulties with regard to small structures of interest or may not show the full three-dimensional context that would facilitate the interpretation of the volumetric image, 49. In particular, small structures may have poor contrast when visualized by these and other techniques known in the art. As a result, the small structures of interest may be easy to miss within the visualized data set. In addition, three-dimensional context may be insufficient for easy interpretation in some viewing modes, such as in slice-by-slice viewing mode. Existing volume rendering methods typically offer only sub-optimal compromises between visualization of the three-dimensional context and contrast of small structures.

I. Volume Rendering Approaches Incorporating Weighting

To improve visualization, a weighting component may be included in the determination of pixel intensity in the rendered image. For example, weighting functions may allow for depth dependence in the determination of intensity values and/or opacity values of voxels of the reconstructed volumetric image 49, which will in turn impact the pixel values in the rendered image. Furthermore, the weighting functions may allow trade offs to be made with regard to image quality, typically the contrast, of a structure of interest and the three-dimensional context associated with the structure. As a result, the operator may increase the contrast of a structure of interest while still maintaining some acceptable or suitable amount of associated context.

A. Zero-Opacity Approaches

For example, equation (1), without the opacity component, may be modified in the following manner:

$$r = \int_a^b w(t)g(t)\,dt, \tag{2}$$

where g is a depth-dependent weighting function. The weighting function allows a compromise between good image contrast and good three-dimensional perception to be reached. For example, weighting functions which may be employed include $g(t)=1-\alpha \cdot |t-t_0|$ or $g(t)=e^{-\alpha \cdot |t-t_0|}$, with $a \leq t_0 \leq b$. These weighting functions allow us to focus on the slice at depth $t_0$, while still showing the three-dimensional context, but with reduced intensity. Alternatively, the weighting function may be specified to be non-symmetric (relative to $t_0$) such as to put more emphasis on structures "in front of", or "behind" the slice at depth $t_0$. In one embodiment, the weighting function allows structures at depth $t_0$ to be viewed in conjunction with some of the three-dimensional context from "behind" that plane, while still maintaining a good contrast of structures at height $t_0$. This may be accomplished by choosing one of the preceding weighting functions, g, defined such that $g(t)=0$ for $t<t_0$. Other weighting functions may be used as well, such as to weight one slice (e.g., at depth $t_0$) or multiple slices, more than other slices. In some cases the weighting function may be set to zero outside of a given interval, thus further focusing the rendering to an even smaller volume of interest.

As one of ordinary skill in the art will appreciate, the depth $t_0$, as used herein, may be associated with the depth of a slice, as indicated in the preceding discussion. In addition, $t_0$ may be associated with other planes or hypersurfaces within the volume of interest 56. For example, $t_0$ may denote the distance from the viewpoint, in which case $t=t_0$ describes a part of a spherical surface, or $t_0$ may denote the distance from the surface of the imaged object.

B. Maximum Intensity Projection Approaches

Equation (2) can also be used as an alternative representation of a maximum intensity projection (MIP) technique in which the weighting function, g, is a delta impulse that is data driven, i.e., the delta impulse may be specified at the location of the maximum intensity along the ray 54. Alternatively, other weighting functions, g, may be employed, such as rectangular pulses, or the previously discussed weighting functions may be employed such that the "location" $t_0$ is determined, for example, by the location of the maximum intensity value along the ray 54. In addition, instead of using the single maximum value along the ray 54, the two (or more) highest values along the ray 54 may be used instead. For example, some function of these two values may be assigned as the pixel value in the rendered image. Since the intensity profiles along rays are typically "smooth", it may be desirable to decompose the intensity profile into several "modes" for processing, such as by interpreting the intensity profile as a linear combination of Gaussians, and to choose the amplitude of the two (or more) largest Gaussians to be combined into the pixel value of the rendered image. Another weighted generalized equation may be expressed as:

$$r = \max{}_{t \in [a,b]} (w(t) \cdot g(t)), \tag{3}$$

which has similar characteristics as MIP but favors values close to a certain height $t_0$ due to the additional weighting function, g. While maximum intensity projection techniques have been discussed, one skilled in the art will readily appreciate that the described approaches may be readily and easily adapted as minimum intensity projection techniques if desired.

C. Opacity Approaches

Equation (2) may be modified to include an opacity weighting function, h, to obtain:

$$r = \int_a^b w(t) \cdot g(t) \cdot e^{-\int_0^t o(s) \cdot h(s)\,ds}\,dt. \tag{4}$$

Either or both of the weighting functions, g and h, may be formulated in accordance with the preceding discussions of the weighting function g or in accordance with different weighting priorities. The addition of a weighting factor, h, for the occlusion term allows structures to be differentially occluded based on their height. For example, structures that are at or above a depth $t_0$ may be more lightly occluded, or not occluded at all, while structures below the depth $t_0$ may be occluded to a greater extent. In this manner, a clearly perceptible occlusion effect caused by structures in the "foreground" may be achieved while still maintaining a significant penetration throughout the volume.

An example of an implementation that may provide good penetration through a volume includes an opacity weighting function, h, that is zero for $t<t_0$, has its maximum at $t=t_0$, and that quickly falls off to zero for $t>t_0$. This opacity weighting function may be used in conjunction with an intensity weighting function, g, that is either small for $t<t_0$, to provide some three-dimensional context in the foreground, or zero for $t<t_0$, and that falls off more slowly relative to h so as to allow sufficient penetration of the volume.

In another implementation, slices or other portions of the volumetric image that are located "behind" and occluded by other slices may be contrast-enhanced, such as by some type of high-pass filtering. In this manner, the three-dimensional perception through the relative motion and the occlusion of different structures is maintained, but the visibility of occluded structures is better preserved. This approach may be further modified to increase or vary the contrast enhancement based on depth. For example, contrast enhancement may be increased as depth increases.

While the preceding discussion provides examples in the form of various equations, one skilled in the art will readily appreciate that such equations are merely intended to be illustrative and not exclusive. Indeed, other equations may also be used to achieve similar effects and are considered to be within the scope of the present technique. Furthermore, though equations (2)–(4) are represented in integral notation for brevity and simplicity, computational implementations of the calculations expressed by equations (2)–(4) may be by discrete approximation of these equations.

In addition, though the present discussion focuses on gray-scale images, the present technique is equally applicable to color images. For example, a weighting function, g and/or h, may associate a different color, as opposed to gray-scale value, with different depths. Applications in color visualization are also considered to be within the scope of the present technique.

II. Viewing Modes Incorporating Weighting Functions

The approaches discussed above generally address the generation of a single rendered image from a three-dimensional volumetric image data set. However, the benefit of volume rendering may be greatly improved through viewing a sequence of rendered images that vary in their viewpoint, view angle, and/or in the volume of interest 56 rendered. In particular, the perceived motion of different structures in a sequence of volume rendered images is a primary contributor to depth perception and to an intuitive understanding of the position and shape of three-dimensional structures within the reconstructed volumetric image 49. The use of weighting functions in the volume rendering process may also have implications for the potential viewing modes used in viewing the resulting sequence of images.

A. Variation of the Volume of Interest

For example, in slice viewing the volume of interest 56, as defined by the start height, a, and the end height, b, is continuously modified to scan through the whole stack of slices. In generalized approaches described herein, the volume of interest 56 may be defined relative to a varying reference height $t_0$ (or vice versa). Alternatively, since the weighting functions g and h can be modified so as to control the start and end-height of the volume of interest 56 as well, it may be sufficient to continuously vary the reference height $t_0$ that controls the "location" or focus of the intensity and opacity weighting functions, while the volume of interest 56, as defined by the start and end heights a and b, encompasses the full reconstructed volume. In this manner, the boundaries of the volume of interest 56 may be defined in terms of depth by controlling the selection of a and b or by having a corresponding cut-off or smooth drop-off in the weighting functions g and h at the corresponding start and end heights.

One can also have lateral boundaries within a volumetric image in the x and y directions which are either hard boundaries or which are implemented as a lateral, possibly smooth, drop-off in the weighting functions g and h. An approach based on weighting may involve the definition of the weighting functions, such as g and/or h, as functions of three variables. By continuously varying the volume of interest 56 in terms of depth and in terms of x and y, one may be able to scan the reconstructed volume in a "telescoping" or selective manner, i.e., focusing on particular volumes of interest, as defined by x, y, and depth, at will. For example, the weighting functions may be defined with a drop-off both in terms of depth as well as laterally. In such an approach, a weighting function may be controlled by centering it around a reference point within the volumetric image 49. The reference point, as one of ordinary skill in the art will appreciate, may be defined by a depth, $t_0$, as well as by x and y coordinates. By varying the coordinates of the reference point, i.e., by "moving" the reference point, one also moves the weighting function and the corresponding cut-off or smooth drop implemented by the weighting function in any of the three-dimensions.

B. Variation of the Viewing Angle

As one of ordinary skill in the art will appreciate, a side view of the tomosynthesis data set generally exhibits relatively poor resolution. For this reason, a systematic variation of the view angle in x and y, such that the view angle 52 remains relatively small, is desirable. For example, in the so-called "tumble view," the view angle describes a circle relative to the x,y plane, where the center of the circle is aligned with the center of the slices of the reconstructed volumetric image 49 or volume of interest 56. The radius of the circle will generally be a function of the depth resolution of the volumetric image data set, which in turn may be a function of the tomosynthesis acquisition geometry.

In some circumstances, artifacts in the reconstructed volumetric image 49 may have a preferred orientation as a function of the acquisition geometry, i.e., the path of the source 12 during the acquisition of the tomosynthesis data set. In these circumstances, other trajectories for the view angle may be desirable to facilitate the apprehension of the three-dimensional structure while minimizing the impact of these orientation dependent artifacts on the visualization process. In particular, other trajectories for the view angle may reduce the occurrence of, the size of, or the intensity of such orientation specific image artifacts. For example, in linear tomosynthesis, where the X-ray source 12 moves along a linear trajectory, the use of an elliptical trajectory for the view angle, where the long axis of the ellipse is aligned with the scanning trajectory of the X-ray source 12, may be beneficial.

C. Combinations of Volume of Interest and Viewing Angle

If the overall volume is too thick to allow a meaningful visualization of the full three-dimensional volume at one time, it may be desirable to vary both the view angle and the volume of interest 56 to improve the display image quality. For example, a spiral tumble or circular tumble with the depth location of the volume of interest 56 changing as the view angle changes may be desirable for thick volumes. In this example, the variation of the depth location of the volume of interest 56, as a function of the view angle, may be constrained such that a 180 degree, i.e., a half-circle, sweep of the view point is associated with movement of the depth location of the volume of interest 56 of less than the thickness of the volume of interest 56. Such a constraint allows every structure to be seen from at least two opposite sides.

D. Simultaneous Display of Images

To better convey the three-dimensional context of the volume, it may be advantageous to display different volume renderings of the same volume in different panes or windows of the display 42 or on separate but proximate displays 42. For example, it may be useful to show a volume rendering from a forward viewpoint and from a backward viewpoint of the same volume of interest 56 or of different volumes of interest 56 that overlap. In such a context, a ray 54 through the center of the volume of interest may be common to both the forward and backward viewpoint, differing only in the ordering of the values along the ray 54. In such an example, both volumes of interest 56 and the associated transfer functions may essentially be "mirror images" of one another with respect to some reference height $t_0$. By simultaneous display of such images, both images can show the same region of the volume in focus while providing three-dimensional context in front of as well as behind this region. Changing the view angle may automatically update the view angle for both views. In addition, by sweeping the height $t_0$ through the volume during viewing, the full volumetric image 49 can be scanned.

In another example, one can have a central rectangular pane or window, with four adjacent panes arranged around the periphery of the central pane. The central pane may show a single rendered image of a volume of interest 56 while the other panes show the same volume of interest 56 from a view angle that is offset by a constant, but adjustable, angle from the view angle used to generate the center image. The direction of the offset may be conveyed by the relative location of a peripheral pane to the central pane, i.e., a pane to the right of center may show an image corresponding to a view angle that is offset to the right, and so forth. In this example, the volume of interest 56 may also be swept through the entire volumetric image data set during viewing so that the full volume may be observed. Similarly, different rendered images may be color coded and superimposed on a single display, as opposed to side-by-side or proximate display.

Alternatively, it may be of interest to simultaneously display volume renderings of the one or more volumes of interest 56 in which various display and/or rendering variables or functions are varied. For example, the same volume of interest 56 may be simultaneously displayed but with different intensity and/or occlusion weighting functions. Alternatively, one or more weighting functions may be constant or identical, but respective transfer functions, such as for determining intensity or occlusion, may be different for the simultaneously displayed renderings. To compare the simultaneously displayed renderings solely on basis of the varied parameters, the volume of interest 56 may be displayed at the same view angle, view geometry, and so forth. Such an approach may be useful for distinguishing or comparing characteristics or structures in the data that may be differentiated based on the varied parameter. For example, some structures of interest may be more easily discerned in a rendering generated using a first set of weighting functions while other structures of interest in the same volume of interest 56 may be more easily discerned in a rendering generated using a second set of weighting functions.

The invention may be susceptible to various modifications and alternative forms, and specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for viewing a sequence of rendered volume images, comprising:
    selecting a volume of interest comprising reconstructed three-dimensional volumetric image data; and
    varying a reference depth affecting the operation of one or more weighting functions used to render volume images representing the volume of interest.

2. The method, as recited in claim 1, wherein the volume of interest encompasses an entire reconstructed volume.

3. The method, as recited in claim 1, wherein varying the reference depth affects the operation of at least one weighting function by changing the location of a cut-off determined from the weighting function.

4. The method, as recited in claim 1, wherein varying the reference depth affects the operation of at least one weighting function by changing the location of a smooth drop-off determined from the weighting function.

5. The method, as recited in claim 1, comprising the step of varying a coordinate in an x,y-plane affecting the operation of the one or more weighting functions, wherein varying the coordinate in the x,y-plane affects the rendering of volume images in the x,y plane and varying the reference depth affects the rendering of volume images in a direction perpendicular to the x,y-plane.

6. The method, as recited in claim 5, wherein varying the coordinate in the x,y-plane affects the operation of at least one weighting function by changing the location of a cut-off determined from the weighting function.

7. The method, as recited in claim 5, wherein varying the at least one coordinate in the x,y-plane affects the operation of at least one weighting function by changing the location of a smooth drop-off determined from the weighting function.

8. The method, as recited in claim 1, wherein at least one weighting function modifies an intensity value.

9. The method, as recited in claim 1, wherein at least one weighting function modifies an opacity value.

10. A computer program, provided on one or more computer readable media, for viewing a sequence of rendered volume images, comprising:
    a routine for selecting a volume of interest comprising reconstructed three-dimensional volumetric image data; and
    a routine for varying a reference depth affecting the operation of one or more weighting functions used to render volume images representing the volume of interest.

11. The computer program, as recited in claim 10, wherein the routine for varying affects the operation of at least one weighting function by changing the location of a cut-off determined from the weighting function.

12. The computer program, as recited in claim 10, wherein the routine for varying affects the operation of at least one weighting function by changing the location of a smooth drop-off determined from the weighting function.

13. The computer program, as recited in claim 10, comprising:
    a routine for varying a coordinate in an x,y-plane affecting the operation of the one or more weighting functions, wherein varying the reference depth affects the rendering of volume images in a first direction and varying the coordinate in the x,y-plane affects the rendering of volume images in a plane perpendicular to the first direction.

14. The computer program, as recited in claim 13, wherein the routine for varying the coordinate in the x,y-plane affects the operation of at least one weighting function by changing the location in the x,y-plane of a cut-off determined from the weighting function.

15. The computer program, as recited in claim 13, wherein the routine for varying the coordinate in the x,y-plane affects the operation of at least one weighting function by changing the location in the x,y-plane of a smooth drop-off determined from the weighting function.

16. The computer program, as recited in claim 10, wherein at least one weighting function modifies an intensity value.

17. The computer program, as recited in claim 10, wherein at least one weighting function modifies an opacity value.

18. A tomosynthesis imaging system, comprising:
an X-ray source configured to emit a stream of radiation through a volume of interest from different position relative to the volume of interest;
a detector array comprising a plurality of detector elements, wherein each detector element may generate one or more signals in response to the respective streams of radiation;
a system controller configured to control the X-ray source and to acquire the one or more signals from the plurality of detector elements;
a computer system configured to receive the one or more signals, to reconstruct a three-dimensional volumetric image data set from the one or more signals, and to render a series of volumes from the three-dimensional volumetric image data set by varying a reference depth affecting the operation of one or more weighting functions used to render each volume; and
an operator workstation configured to display the series of volumes.

19. The tomosynthesis imaging system, as recited in claim 18, wherein varying the reference depth affects the operation of at least one weighting function by changing the location of a cut-off determined from the weighting function.

20. The tomosynthesis imaging system, as recited in claim 18, wherein varying the reference depth affects the operation of at least one weighting function by changing the location of a smooth drop-off determined from the weighting function.

21. The tomosynthesis imaging system, as recited in claim 18, wherein the computer system is further configured to render the series of volumes by varying a coordinate in an x,y-plane affecting the operation of the one or more weighting functions, wherein varying the coordinate in the x,y-plane affects the rendering of volumes in the x,y-plane and varying the reference depth affects the rendering of volumes in a direction perpendicular to the x,y-plane.

22. The tomosynthesis imaging system, as recited in claim 21, wherein varying the coordinate affects the operation of at least one weighting function by changing the location of a cut-off determined from the weighting function.

23. The tomosynthesis imaging system, as recited in claim 21, wherein varying the coordinate affects the operation of at least one weighting function by changing the location of a smooth drop-off determined from the weighting function.

24. The tomosynthesis imaging system, as recited in claim 18, wherein at least one weighting function modifies an intensity value.

25. The tomosynthesis imaging system, as recited in claim 18, wherein at least one weighting function modifies an opacity value.

26. A tomosynthesis imaging system, comprising:
means for selecting a volume of interest comprising reconstructed three-dimensional volumetric image data; and
means for varying a reference depth affecting the operation of one or more weighting functions used to render volume images representing the volume of interest.

27. A method for viewing a sequence of rendered volume images, comprising:
selecting a volume comprising reconstructed three-dimensional volumetric image data; and
varying a view angle for rendering volume images of the volume such that the visual presence of one or more orientation specific image artifacts is reduced.

28. The method, as recited in claim 27, wherein varying the view angle comprises varying the view angle along an elliptical trajectory such that the long axis of the elliptical trajectory corresponds to a linear scanning trajectory of an X-ray source.

29. A computer program, provided on one or more computer readable media, for viewing a sequence of rendered volume images, comprising:
a routine for selecting a volume comprising reconstructed three-dimensional volumetric image data; and
a routine for varying a view angle for rendering volume images of the volume such that the visual presence of one or more orientation specific image artifacts is reduced.

30. The computer program, as recited in claim 29, wherein the routine for varying the view angle varies the view angle along an elliptical trajectory such that the long axis of the elliptical trajectory corresponds to a linear scanning trajectory of an X-ray source.

31. A tomosynthesis imaging system, comprising:
an X-ray source configured to emit a stream of radiation through a volume of interest from different position relative to the volume of interest;
a detector array comprising a plurality of detector elements, wherein each detector element may generate one or more signals in response to the respective streams of radiation;
a system controller configured to control the X-ray source and to acquire the one or more signals from the plurality of detector elements;
a computer system configured to receive the one or more signals, to reconstruct a three-dimensional volumetric image data set from the one or more signals, and to render a series of volumes from the three-dimensional volumetric image data set by varying a view angle such that the visual presence of one or more orientation specific image artifacts is reduced in the series of volumes; and
an operator workstation configured to display the series of volumes.

32. The tomosynthesis imaging system, as recited in claim 31, wherein the computer system is configured to vary the view angle along an elliptical trajectory such that the long axis of the elliptical trajectory corresponds to a linear scanning trajectory of the X-ray source.

33. A tomosynthesis imaging system, comprising:
means for selecting a volume comprising reconstructed three-dimensional volumetric image data; and
means for varying a view angle for rendering volume images of the such that the visual presence of one or more orientation specific image artifacts is reduced.

* * * * *